(12) United States Patent
Rund et al.

(10) Patent No.: US 7,566,168 B2
(45) Date of Patent: Jul. 28, 2009

(54) APPARATUS AND METHOD FOR DETERMINING THE AMOUNT OF TIME UNTIL A DESIRED TEMPERATURE IS REACHED

(75) Inventors: Richard Rund, Great Falls, VA (US); Pierre Charlety, Deng Chau (CN); Ma Huai Wang, Zhaoqing (CN); Quan Zhi Yong, Rongcheng Town, HeNan Province (CN)

(73) Assignee: Shake Awake Products, LLC

( * ) Notice: Subject to any disclaimer, the term of this patent is extended or adjusted under 35 U.S.C. 154(b) by 2 days.

(21) Appl. No.: 11/684,491

(22) Filed: Mar. 9, 2007

(65) Prior Publication Data

US 2008/0056328 A1 Mar. 6, 2008

Related U.S. Application Data

(63) Continuation-in-part of application No. PCT/US2006/032951, filed on Aug. 21, 2006, which is a continuation-in-part of application No. 11/428,260, filed on Jun. 30, 2006, now abandoned.

(60) Provisional application No. 60/780,830, filed on Mar. 10, 2006, provisional application No. 60/709,446, filed on Aug. 19, 2005, provisional application No. 60/806,901, filed on Jul. 10, 2006, provisional application No. 60/884,411, filed on Jan. 10, 2007.

(51) Int. Cl.
*G01K 13/00* (2006.01)
*G01K 3/00* (2006.01)

(52) U.S. Cl. .................. 374/102; 374/107; 374/163; 374/45; 374/141

(58) Field of Classification Search ............... 374/102, 374/163, 141, 107, 45
See application file for complete search history.

(56) References Cited

U.S. PATENT DOCUMENTS

| | | | | |
|---|---|---|---|---|
| 4,358,932 A | * | 11/1982 | Helfrich, Jr. | 62/126 |
| 4,587,405 A | * | 5/1986 | Andre | 219/491 |
| 7,102,107 B1 | * | 9/2006 | Chapman | 219/494 |
| 2007/0215599 A1 | * | 9/2007 | Kahler | 219/492 |

FOREIGN PATENT DOCUMENTS

GB 2206222 A * 12/1988

* cited by examiner

*Primary Examiner*—Gail Verbitsky
*Assistant Examiner*—Mirellys Jagan
(74) *Attorney, Agent, or Firm*—General Counsel, P.C.

(57) ABSTRACT

A method and an apparatus capable of determining the amount of time remaining before an item such as food reaches a desired temperature such as a cooking temperature or approximately room temperature. In at least one embodiment, determining the amount of time remaining is based at least on the elapsed time and the percentage of temperature range between a first temperature and the desired temperature completed or remaining to be covered.

46 Claims, 11 Drawing Sheets

APPARATUS AND METHOD FOR DETERMINING THE AMOUNT OF TIME UNTIL A DESIRED TEMPERATURE IS REACHED

This patent application is a continuation-in-part application of PCT application no. PCT/US2006/032591 filed on Aug. 21, 2006, which designated the U.S. and was a continuation-in-part application of U.S. patent application Ser. No. 11/428,260 filed on Jun. 30, 2006 now abandoned, which claims the benefit of U.S. Provisional patent application No. 60/780,830 filed on Mar. 10, 2006 and U.S. Provisional patent application No. 60/709,446 filed on Aug. 19, 2005. PCT application no. PCT/US2006/032951 claims the benefit of U.S. Provisional patent application No. 60/709,446 filed on Aug. 19, 2005, U.S. Provisional patent application No. 60/780,830 filed on Mar. 10, 2006, U.S. Provisional patent application No. 60/806,901 filed on Jul. 10, 2006.

This patent application is a continuation-in-part application of U.S. patent application Ser. No. 11/428,260 filed on Jun. 30, 2006, which claims the benefit of U.S. Provisional patent application No. 60/780,830 filed on Mar. 10, 2006 and U.S. Provisional patent application No. 60/709,446 filed on Aug. 19, 2005.

This patent application claims the benefit of U.S. Provisional patent application No. 60/884,411 filed on Jan. 10, 2007, U.S. Provisional patent application No. 60/806,901 filed on Jul. 10, 2006, and U.S. Provisional patent application No. 60/780,830 filed on Mar. 10, 2006.

I. FIELD OF THE INVENTION

This invention relates to the calculation of the time remaining before a desired temperature is reached for food or a similar item. The desired temperature can be, for example, the cooking temperature for a food or the room temperature.

II. BACKGROUND OF THE INVENTION

Most food safety recommendations are for cooking foods to particular temperatures based on the identity of the food item. This requires that the user periodically check the temperature of the food being cooked to see if the desired temperature has been reached, and depending upon the recommendation being used, begin a timer for a period of time while keeping the food at the particular temperature for that time period.

Most recipes on the other hand are for cooking a food for a particular time period in an environment of a certain temperature on the theory that the food being cooked will reach the needed temperature shortly before or at the expiration of the time period. This approach cause problems, because the oven or other cooking device typically do not obtain the correct cooking temperature or the user does not provide sufficient heat to the food, for example, during stove top cooking or grilling.

Today given the increase in utility costs, it is desirable to not place a hot food directly into the refrigerator. In addition, however, if a food remains out in or at room temperature for to long or is in the temperature range of 70° F. to 140° F. for over two hours, then a variety of bacteria will start to grow that may cause food borne illnesses for the consumers of the food.

III. SUMMARY OF THE INVENTION

This invention provides a method and an apparatus for determining the amount of time remaining for an item to reach a desired temperature.

The invention in at least one embodiment includes a method for predicting the time for an item to reach a desired temperature, the method includes obtaining a desired temperature, beginning an elapsed timer, determining a current temperature of an item, and calculating the predicted time until the item reaches the desired temperature based on the value of the elapsed timer and the percentage of temperature range between a first determined temperature and the desired temperature remaining to be covered.

The invention in at least one embodiment includes a method for predicting the time for an item to reach a desired temperature, the method includes obtaining a desired temperature, beginning an elapsed timer, determining a current temperature of an item, and calculating the predicted time until the item reaches the desired temperature based on the value of the elapsed timer and the percentage of temperature range between a first temperature and the desired temperature completed.

The invention in at least one embodiment includes a method comprising obtaining a desired temperature, beginning an elapsed timer, determining a current temperature of food being cooled, and calculating the predicted cooling time for food to reach the desired temperature based at least on the value of the elapsed timer and the current temperature.

The invention in at least one embodiment provides a notification if food has cooled or will cool to long of a time period through a temperature range likely to cause food borne illnesses. One exemplary situation is having food cool longer than two hours between 140° F. and 70° F. or between 135° F. and 70° F.

The invention in at least one embodiment includes a system having a probe having a temperature sensing component; a display; temperature means for converting a signal from the temperature sensing component into a temperature; predicting means for predicting a time remaining to reach a desired temperature based upon a temperature difference between the temperature generated by the temperature means and the desired temperature; and controlling means for controlling the display to show the predicted time remaining.

Given the following enabling description of the drawings, the apparatus should become evident to a person of ordinary skill in the art.

IV. BRIEF DESCRIPTION OF THE DRAWINGS

The aspects of the present invention will become more readily apparent by describing in detail illustrative, non-limiting embodiments thereof with reference to the accompanying drawings.

V. DETAILED DESCRIPTION OF THE DRAWINGS

The invention includes methods and apparatuses for determining the amount of time remaining before food (or other item that requires heating and/or cooling) reaches a desired temperature as a result of heating and/or cooling, i.e., predicted heating and/or cooling time. In embodiments where the item is being heated, the invention provides information regarding the time remaining to cook the food to a desired temperature. In embodiments where the item is being cooled, the invention provides information regarding the time until the food cools to a desired temperature, for example, room temperature, a preset approximation for room temperature, or 70° F.

Figure 1:
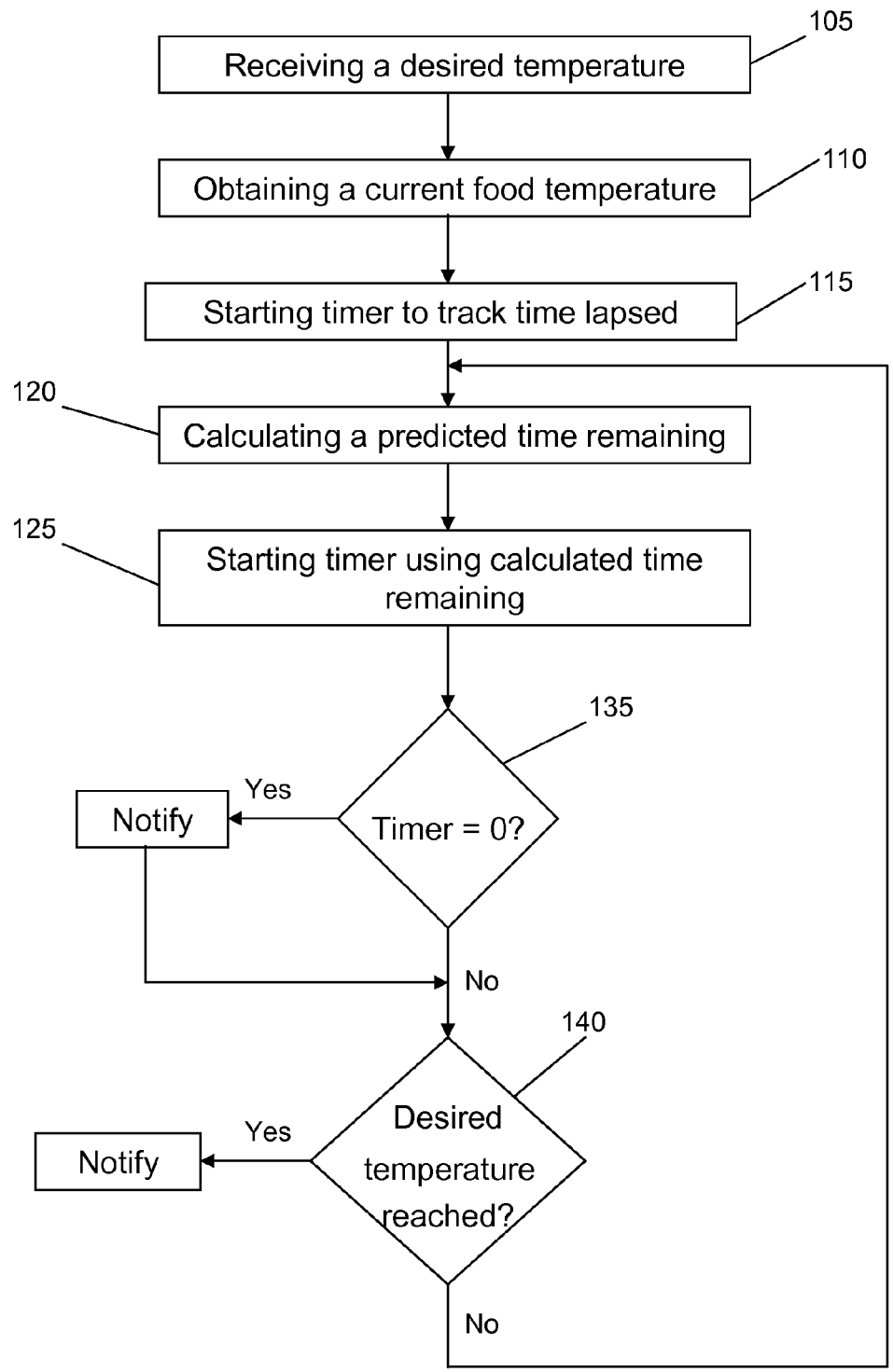
FIG. 1 illustrates an exemplary method according to the invention.

FIG. 1 illustrates an exemplary method for predicting the time remaining before a desired temperature is reached. The illustrated method begins with obtaining (or receiving) a desired temperature for the food, 105, and determining (or obtaining) the current temperature of the food, 110. Exemplary ways to obtain the desired temperature includes receiving a desired temperature from the user, determining a desired temperature based on information (for example, meat type, level of doneness, or other characteristics of the item) entered by the user, determining the temperature of the environment for cooling, and retrieving the temperature from memory, for example, as a preset temperature or a stored environment temperature prior to heating. Steps 105 and 110 may be performed in any order or substantially concurrently with each other. Prior to cooking, a timer (or elapsed timer) is started to track the time that the item is being heated, 115. However, if the item is being cooled, then the timer is preferably initiated just after the item is removed from the heat source, e.g., an oven or stove, or after the food item has cooled to a specified temperature threshold. In this manner, the timer tracks the time that the item is cooled. In some exemplary embodiments, this time may be displayed.

In step 120, calculating the predicted time remaining for the item to reach the desired temperature, for example, is preferably based on the ratio of percentage to go to percentage completed with respect to temperature for the item. An exemplary formula for the remaining time ($t_R$) is $$t_R = \frac{t}{\% \text{ completed}} \times \% \text{ to go}$$

wherein $$\% \text{ to go} = \left(\frac{T_D - T_2}{T_D - T_1}\right)$$

$$\% \text{ completed} = 1 - \% \text{ to go} = 1 - \left(\frac{T_D - T_2}{T_D - T_1}\right)$$

An exemplary formula for calculating the predicted time then is $$t_R = \frac{t}{1 - \left(\frac{T_D - T_2}{T_D - T_1}\right)} \times \left(\frac{T_D - T_2}{T_D - T_1}\right)$$

In the formula, $t_R$ equals the time to reach the desired temperature and this is the time that is used to provide the new starting point for a timer (or countdown timer) on the display, 125. $T_D$ represents the desired temperature, $T_1$ equals the temperature at the start (or first determined temperature), and $T_2$ equals the current temperature with t equaling the time as tracked by the timer started in 115.

Figure 2:
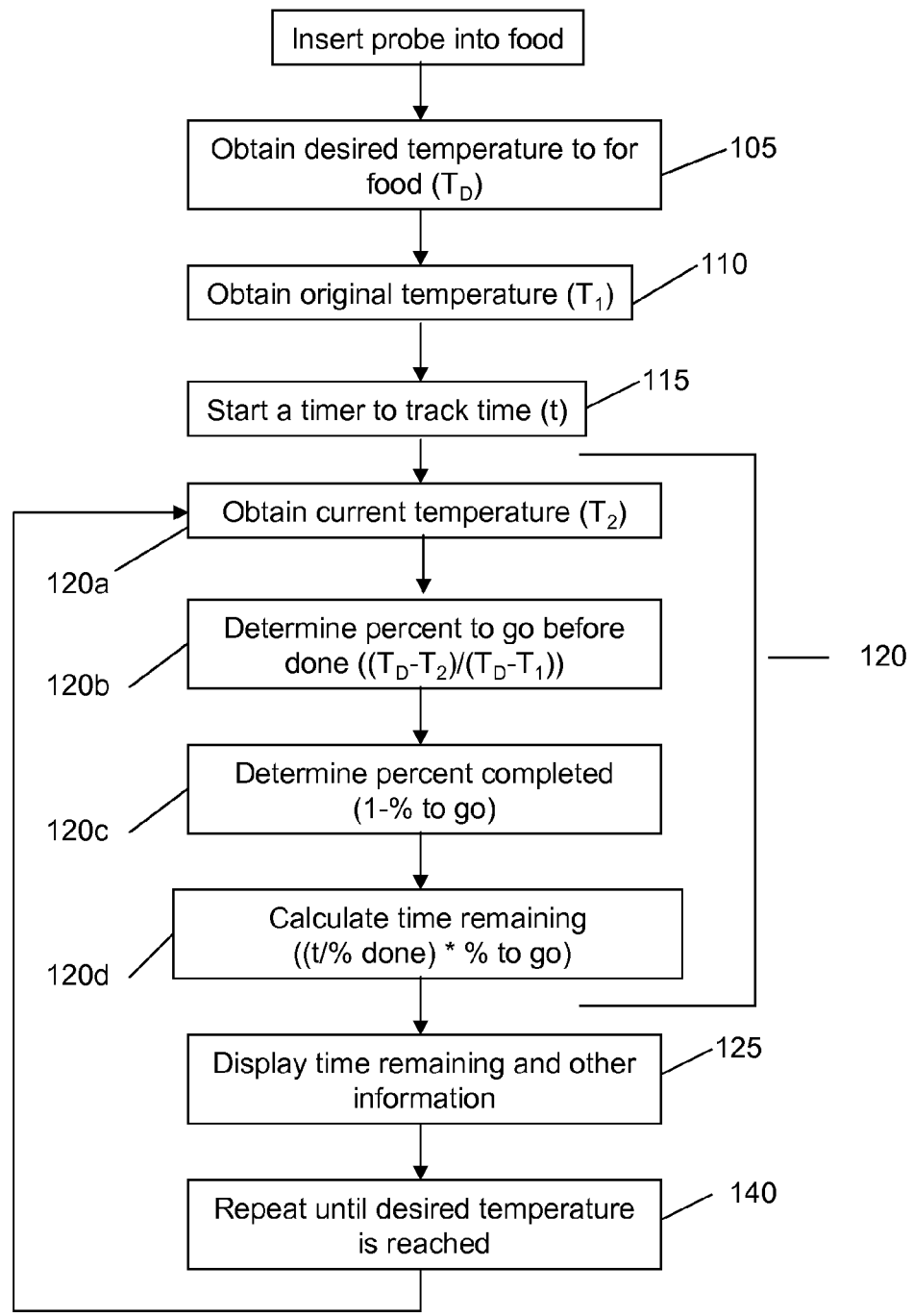
FIG. 2 illustrates an exemplary method according to the invention.

FIG. 2 includes an exemplary way to determine the time remaining before the desired temperature is reached using the above formula. The current temperature ($T_2$) is obtained, 120a. In one embodiment, step 110 is omitted in favor of step 120a. The percentage to go before the desired temperature ($T_D$) is reached is determined, 120b. The percentage completed is determined based on the percentage to go, 120c. The time remaining before the desired temperature is reached is determined based on the calculated percentages (i.e., % to go and % completed) and the time (t), 120d.

The initial calculation of the time prediction can occur over a variety of time and/or ranges of remaining percentages including delaying the initial determination for a period of time. In a cooling situation, the initial prediction can be based on the time it takes the item to go from, for example, the high recorded temperature to a lower temperature, which could be delayed for a predetermined time or decrease in temperature.

When the timer reaches zero, an alarm sounds or other notification occurs to let the cook know that the food is predicted as having reached the desired temperature, 135. This timer alarm/notification is superseded when the temperature reaches the desired temperature for the food, notifying the cook that the food is ready, for example, by displaying "DONE" on the display, 140. The display may flash the exemplary word notification or display the text without flashing. Other exemplary notifications include sounding an audio alarm, flashing a visual cue such as a light, and any other type of timer notifications. In at least one embodiment, only one notification is provided. In some embodiments, notification is not provided or just one type of notification is provided.

The timer displays the remaining time to reach the desired temperature. The method in at least one exemplary embodiment encompasses displaying the time as hours:minutes:seconds, minutes:seconds, and switching between the two displays at a predetermined time junction and/or allowing the cook to switch between the display options.

In the exemplary method illustrated in FIG. 1, 120 through 140 are repeated for each sampling period. Exemplary sampling periods are any amount of time between 1 second and 120 seconds including the end points. In other exemplary embodiments, the sample period is selected from 5, 10, 20, 30, 40, 45, and 60 seconds. The sampling periods in at least one exemplary embodiment are selected from a range of 0 to 300 seconds; however, the sampling period may be any length of time. Current U.S. Department of Agriculture recommendations are for at least 15 seconds hold time at the desired cooking temperature. The sampling period also may vary during the process by becoming more frequent as the current temperature approaches the desired temperature. In one embodiment, instead of starting a countdown timer, the predicted time remaining is displayed.

Figure 3:
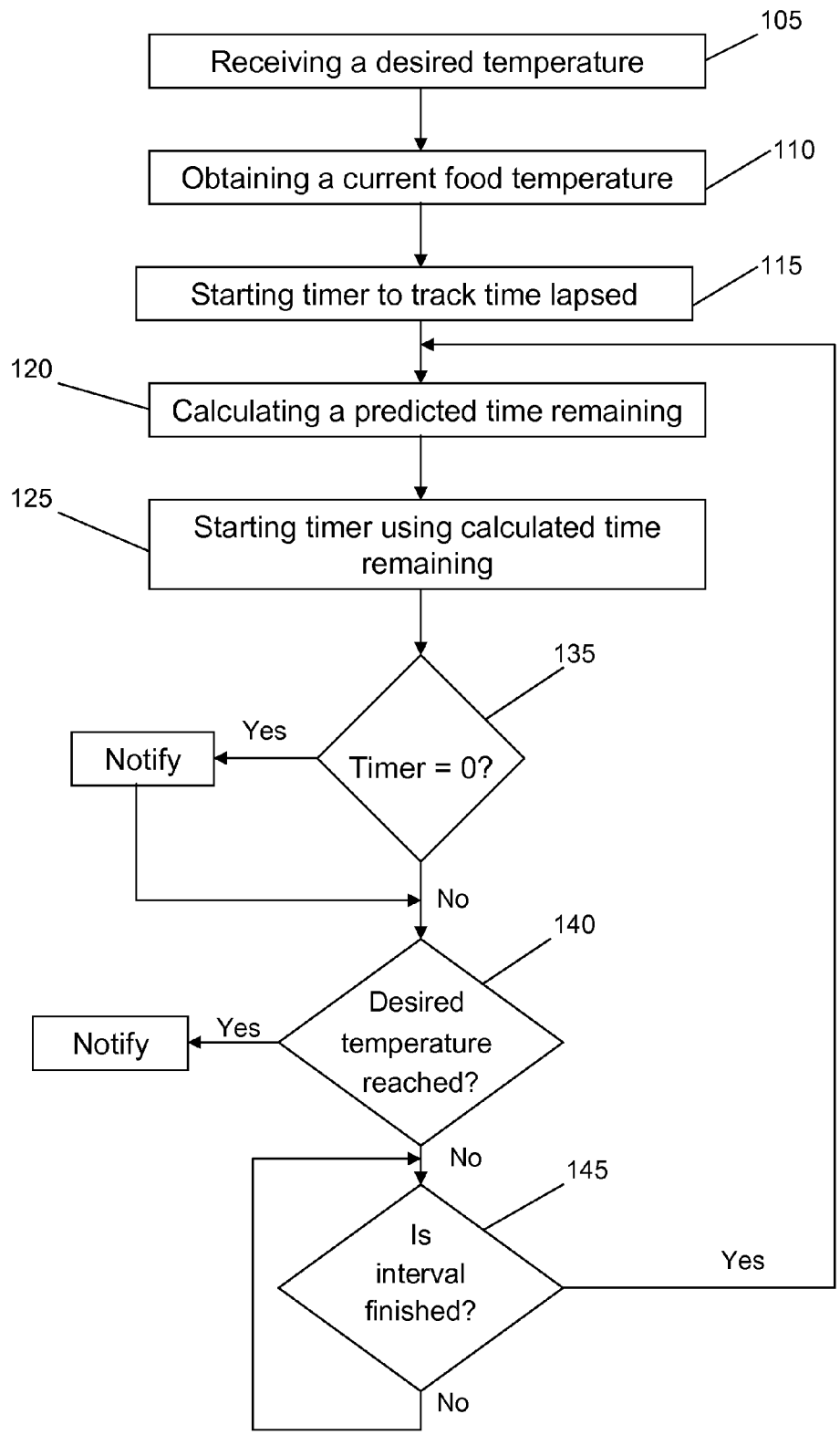
FIG. 3 illustrates an exemplary method according to the invention.

As illustrated in FIG. 3, other exemplary embodiments instead of having a continual sampling of the temperature perform the sampling at predetermined time intervals, 145, for example, every 5 or 10 minutes. An exemplary way to accomplish time intervals is by using counters or similar mechanisms.

Another exemplary embodiment uses a sampling period that is determined by taking a predetermined percentage of the remaining time. This calculation of sampling time based on percentage continues until the remaining time has reached a predetermined threshold such as 20 seconds or 1 minute.

In other exemplary embodiments, the sampling period is based on a predetermined change in temperature (instead of time as illustrated in FIG. 3), for example, 5°, 10°, or 20° or percentage change in temperature.

An alternative approach is to use the change in rates of temperature change to provide for an increasing/decreasing rate of temperature change of the food as it gets closer to the desired temperature.

Figure 4:
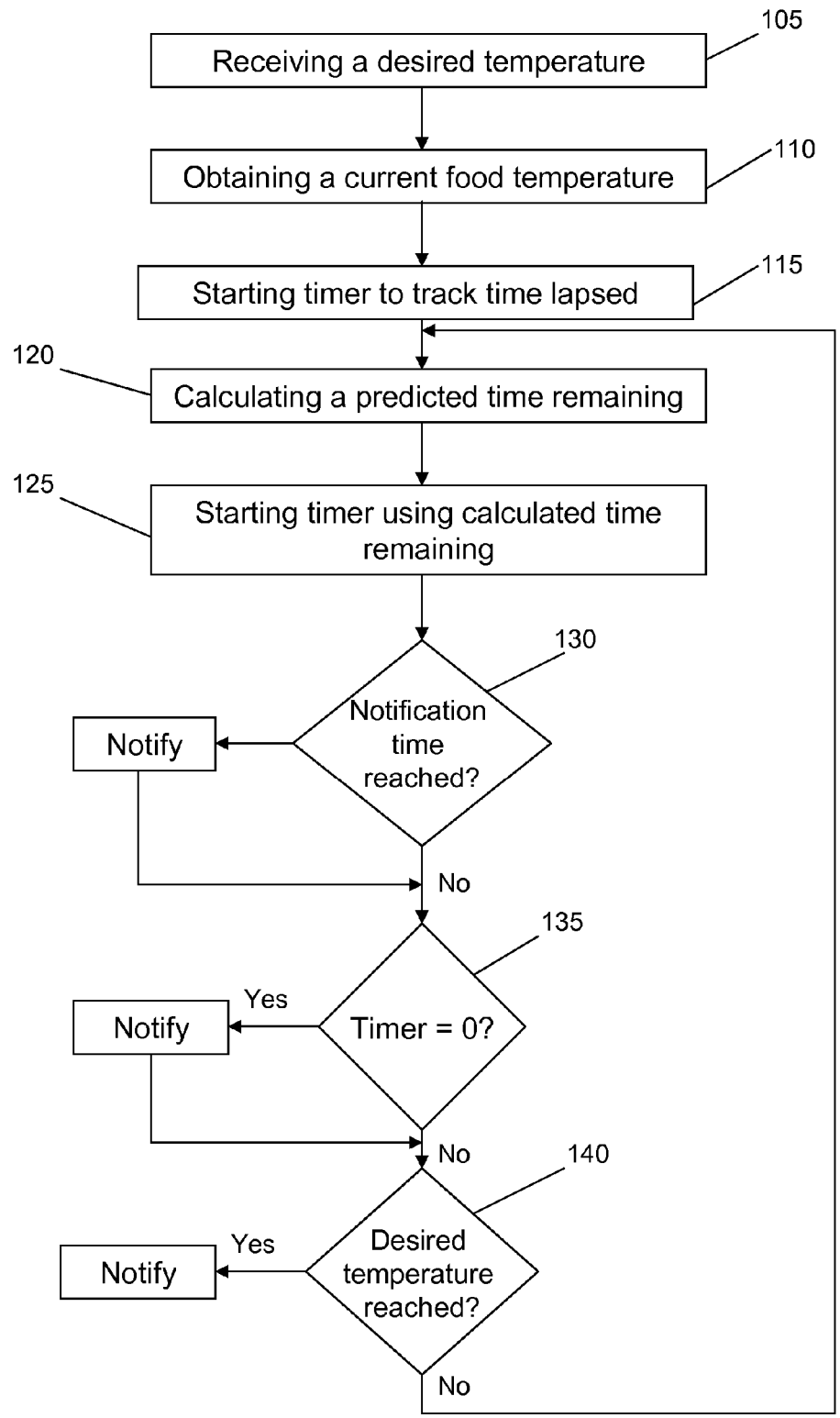
FIG. 4 illustrates an exemplary method according to the invention.

The exemplary method illustrated in FIG. 4 adds a notification to the cook at a predetermined amount of time remaining for the food to reach the desired temperature, 130. The notification typically is an audio announcement or alarm, but may be a visual cue such as a flashing light (or display) or notification on the display. An exemplary time to notify the cook is in a range of 0 to 20 minutes. In at least one exemplary embodiment the notifications occur at different times and are of different character to allow the cook to have a countdown other than the timer to the food reaching the desired temperature, which will assist in cooking other foods and have them done at approximately the same time.

In an exemplary embodiment for heating an item and where it is desired to not display the temperature below a certain temperature, the display may provide a general representation of the temperature and in at least one exemplary embodiment also not provide the remaining time to until the desired temperature is reached. For example, if the temperature is below 75° F., then the display shows COOL or some other indicator. Another example is when the item has a temperature between 75° F. and 100° F., the display shows WARM or some other indicator. Another example is to display an arrow(s) pointing up on the display to indicate increasing temperature. When the desired temperature has been reached, displaying DONE or similar words and in some exemplary embodiments having an audio alert. A variety of other words may be displayed to indicate the temperature, including the temperature itself. The particular temperature ranges may be adjusted for a particular implementation.

In an exemplary embodiment for cooling an item and where it is desired to not display the temperature, the display may provide an indication that cooling is occurring for example with COOL, DOWN, COOLING, and/or an arrow(s) pointing down on the display. Another exemplary display is to alternate between COOL and DOWN. The display in at least one exemplary embodiment flashes to provide further indication that the food is being cooled. When the temperature is within a predetermined range of the desired temperature, for example, 5 degrees, the display provides a notification to the user including, for example, a message such as DONE or REF for an indication to put the item into the refrigerator.

In an exemplary embodiment, the display will show WAIT between the time when the alarm is turned off from a heating time prediction and prior to starting a cooling time prediction.

In at least one exemplary embodiment where cooling time is predicted, the prediction is based on tracking the time that the item is cooling from a threshold temperature. Examples of a threshold temperature include the high temperature reached, the desired temperature, a temperature offset from the high or desired temperature by a percentage amount or predetermined number of degrees, or a temperature derived from industry or government standards (for example, 135° F. or 140° F.). The desired temperature for cooling includes room temperature, room temperature plus a few degrees (for example, 5° F.) to add an additional food safety margin, an approximation for room temperature (for example, a temperature selected from the range of 65° F. to 85° F.), or an industry or government standard (for example, 70° F.). An exemplary source of government standards includes those issued by the U.S. Department of Agriculture.

Figure 5:
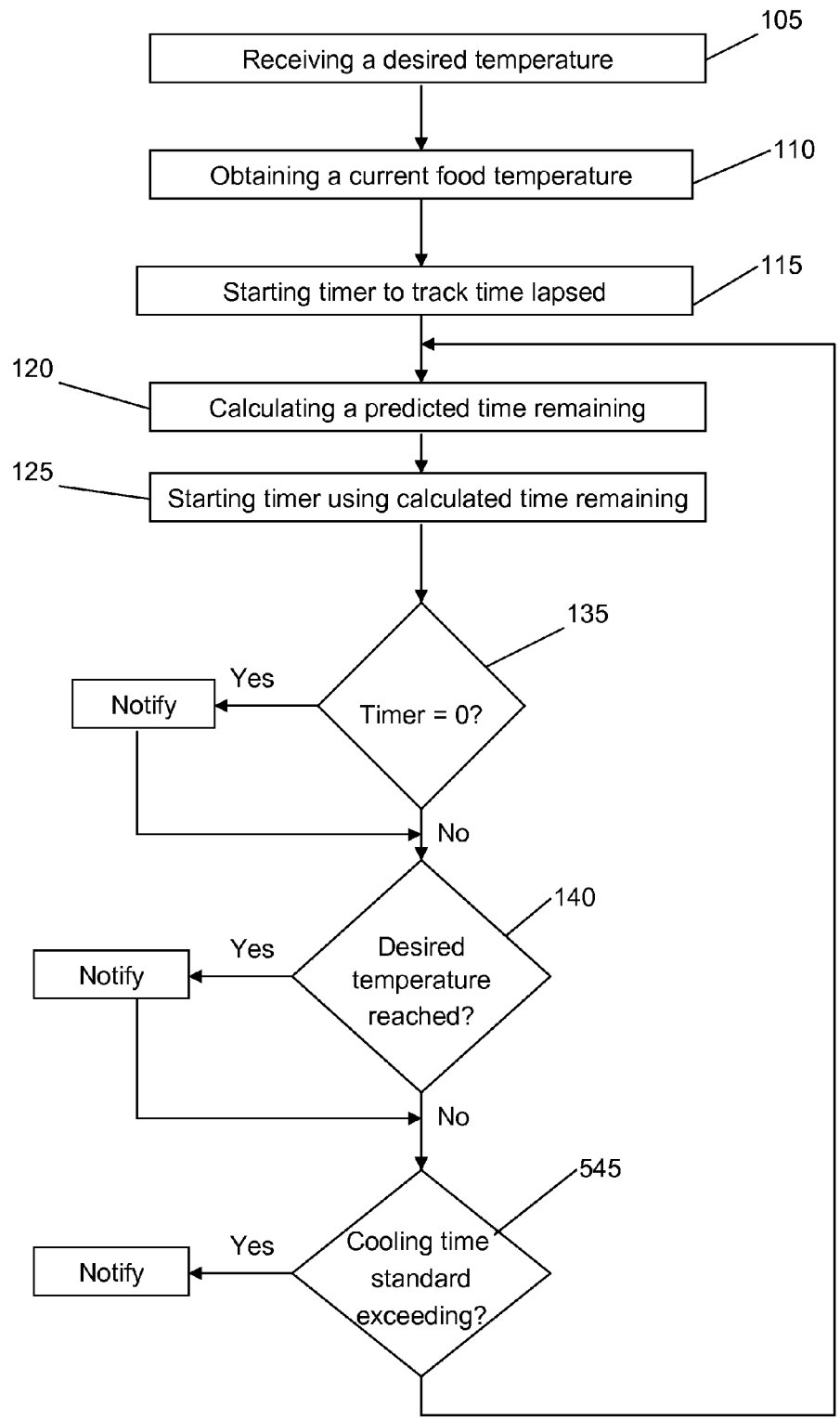
FIG. 5 illustrates an exemplary method according to the invention.

In at least one embodiment illustrated in FIG. 5, the method includes notifying the user, 545, if the desired cooling time period is exceeded, or predicted to be exceeded, to allow the user to take appropriate measures with respect to the item such as disposing of it or refrigerating it. One exemplary way is to time the cooling period from a threshold temperature and when the food has not reached the desired temperature in the time provided for in the standard, to notify the user. Another exemplary way is that when the cooling time from a threshold temperature added to the predicted time remaining to reach the desired temperature is greater than the time provided for in the standard, notifying the user so that the food may be chilled. In at least one exemplary embodiment, the method sets the desired temperature as the higher of a) 70° F. (or other standard set temperature) or b) room temperature or room temperature plus a few degrees, for example, five degrees.

Using temperatures derived from the U.S. Department of Agriculture recommendations, the method in a cooling embodiment as illustrated in FIG. 5 tracks the time to cool to determine if it is within food safety ranges, for example, that the food drops from 140° F. to room temperature plus five degrees (or 70° F.) within two hours. If the two hour time period is exceeded, the user is preferably notified of this so that the food can be disposed of or otherwise dealt with. Another exemplary embodiment adds the time that the item has cooled with the predicted time remaining to cool to see if it exceeds the two hours or other criteria, and if it does then notifying the user so that the food can be cooled in a refrigerator or other cooling method to more quickly drop the temperature. In one embodiment, an alarm is provided at the two hour mark as a safety feature to remind the cook to attend to the food item, e.g., refrigerate the food item or serve the food item.

In an exemplary embodiment where the device includes both the time remaining to heat and the time remaining to cool, the device allows the user to select the mode to be used with activation of a button and/or switch. As such the exemplary methods can include receiving the selection of the operation mode. In one embodiment, when the change occurs the desired temperature becomes a desired cooling temperature that is predetermined, received from the user, or based on a room temperature reading.

Alternatively, the device may automatically switch from time remaining to heat to time remaining to cool when the desired heating temperature has been reached and there has been a predetermined decrease from the high temperature reached. For example, if the desired temperature was 200° F. and once the item was removed it continued to heat itself from the heat stored in the container to a temperature of 215° F., when the temperature of the item dropped from 215° F. by a predetermined amount the time remaining to cool feature would begin. Alternatively, the predetermined temperature drop may be from the desired temperature. The predetermined amount may be a set temperature change such as 5° F. or 10° F. or a percentage drop in temperature. An exemplary method will include the additional steps of monitoring the temperature until it reaches its high point, recording that temperature, then monitoring the temperature change until the predetermined amount has been reached, and beginning the method to track time remaining by obtaining the desired temperature. In at least one embodiment, a manual switch is provided to allow the user to change from time remaining to heat to time remaining to cool in advance of or in lieu of the automatic switch.

In a further exemplary method, the probe can be calibrated when inserted into an ice bath. When the probe detects a temperature in a first range, for example, 29° F. to 35° F., the probe will notify the user of this and give the user the opportunity to activate a calibration routine that sets the temperature to 32° F. and records the error value so that future temperature readings are adjusted in view of this error value. In one embodiment, the first range is any range that includes 32° F. Another calibration can occur for a device with two probes, such that when they are within a predetermine range of each other the user is given the opportunity to set one probe to equal the other probe.

The cooling time remaining for an item in other exemplary embodiments may be determined in other ways than that described above. One exemplary embodiment for step 120 is calculating the predicted time remaining for cooling based on the current rate of temperature change for the item. An exemplary way to predict the time is to calculate the remaining difference in temperature and dividing it by the current rate of temperature change over the last sampling period, which as discussed above can be based on any of a variety of conditions. Exemplary formulas using rate of change of the temperature determining the time remaining include $$t_R = \left(\frac{T_D - T_2}{T_2 - T_1}\right) \times (t_2 - t_1)$$

$$t_R = \left(\frac{T_D - T_1}{T_2 - T_1}\right) \times (t_2 - t_1) + t_1 - t_2$$

$$t_R = \left(\frac{T_2 - T_D}{T_1 - T_2}\right) \times (t_2 - t_1)$$

$$t_R = \left(\frac{T_1 - T_D}{T_1 - T_2}\right) \times (t_2 - t_1) + t_1 - t_2$$

In the equations, $t_R$ equals the cooling time to reach the desired temperature and this is the time that is used to provide the new starting point for the timer on the display, 125. $T_D$ represents the desired temperature, $T_1$ equals the temperature at the start of the sampling, and $T_2$ equals the temperature at the end of the sampling with $t_1$ and $t_2$ equaling the respective times of the temperature sampling. Alternatively, $T_1$ and $t_1$ may be the starting temperature and zero, respectively. As discussed above, the desired temperature ($T_D$) for cooling can be based on a variety of temperatures including preset and actual readings.

The above formulas in one embodiment are supplemented for the situation where there is a sudden increase in food temperature during the cooling. The rate of temperature change ($T_{RC}$) prior to the higher temperature being recorded is used, and the following representation can be used $$T_{RC} = \left(\frac{t_2 - t_1}{T_2 - T_1}\right)$$

$T_1$ equals the temperature at the start of the prior sampling that gave rise to this situation, $T_2$ equals the temperature at the end of the prior sampling with $t_1$ and $t_2$ equaling the respective times of the temperature sampling. To adjust for this situation, the following exemplary equation may be used $$t_R = \frac{T_D - T_C}{T_{RC}} = \left(\frac{T_D - T_C}{T_2 - T_1}\right) \times (t_2 - t_1)$$

where $T_D$ equals the desired temperature and $T_C$ equals the current temperature. This exemplary method will record the rate of temperature change and continue to use it when the current temperature increases above the previous temperature during cooling.

Another exemplary way to calculate the predicted time remaining for the item to reach the desired temperature is based on the ratio of percentage completed to percentage to go with respect to temperature for the item. An exemplary formula for the remaining time ($t_R$) is $$t_R = \frac{t}{\% \text{ completed}} \times \% \text{ to go}$$

wherein $$\% \text{ completed} = \left(\frac{T_1 - T_2}{T_1 - T_D}\right)$$

$$\% \text{ to go} = 1 - \% \text{ to completed} = 1 - \left(\frac{T_1 - T_2}{T_1 - T_D}\right)$$

In the equation, $t_R$ equals the time to reach the desired temperature and this is the time that is used to provide the new starting point for the timer on the display, 125. $T_D$ represents the desired temperature, $T_1$ equals the temperature at the start, and $T_2$ equals the temperature at the end of the sampling with t equaling the time as tracked by the timer started in 115. The exemplary way to calculate the remaining time becomes the following exemplary formula $$t_R = \frac{t}{\left(\frac{T_1 - T_2}{T_1 - T_D}\right)} \times \left(1 - \left(\frac{T_1 - T_2}{T_1 - T_D}\right)\right)$$

As discussed above, the desired temperature ($T_D$) for cooling can be based on a variety of temperatures including preset and actual readings. Likewise, the starting temperature ($T_1$) can be based on a variety of temperatures including preset and actual readings as discussed above. The temperature differential in temperature readings divided by the temperature difference from the initial temperature to the desired temperature represents a percent cooled, and in a heating embodiment this would represent a percentage heated.

Figure 6:
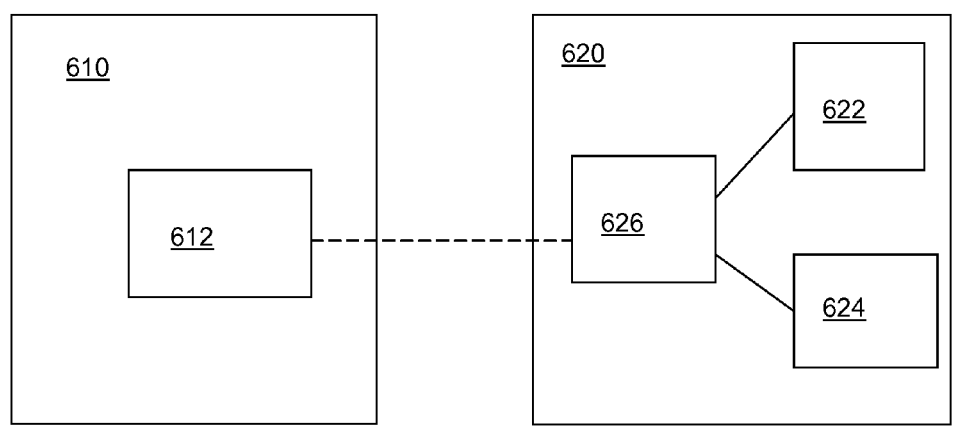
FIG. 6 illustrates a block diagram of an exemplary embodiment according to the invention.

An exemplary system for performing the different exemplary methods is illustrated in FIG. 6. The illustrated system includes a probe 610 and a base unit 620. The probe 610 and the base unit 620 can be connected directly together, connected via a wire, or in wireless communication. If the probe 610 and the base unit 620 are connected via a wire then the wire preferably is flat (or small diameter) to lessen the impact on the seal of the oven for embodiments intended for oven use or other sealed environments. The wire, depending upon the implementation, is detachable from the main unit 620, which then would include a port or other socket for connection to a plug or other connector on the wire.

The probe 610 includes a temperature sensing component 612. The probe 610 in a wireless configuration includes a transmitter for communicating with the base unit 620. The probe 610 in at least one embodiment includes a pointed tip.

The base unit 620 as illustrated includes a display 622, an interface 624, and thermometer circuitry 626 in communication with the temperature sensing component 612. In a wireless configuration, the base unit 620 includes a receiver for communicating with the probe 610.

The display 622 is preferably a liquid crystal display (LCD), but may be any other type of display that is capable of displaying text or image data information to a user. Exemplary types of other displays include a plasma screen, LEDs, and projection systems. As discussed in connection with the exemplary configurations illustrated in FIGS. 11-15, the display 622 can display the remaining time until the desired temperature is reached, the desired temperature, the length of time that heating/cooling has been occurring, the current temperature reading of the food, a taste setting and the type of food being cooked. Some of the display items may be user selectable as to whether they are displayed or to what extent they are displayed.

The interface 624 receives user input for the thermometer circuitry 626 and, in some exemplary arrangements, the information shown on the display 622. The interface 624 provides an interface for the user to input data into the base unit 620 and may include any number of inputs, such as dials, buttons or keys that allow a user to input a pre-determined or desired cooking temperature and perform other functions necessary for operation of the device. The interface 624 in at least one embodiment includes a dial that can be used to select and/or set one or more of the parameters shown on the display 622. Further exemplary interfaces are discussed below in connection with exemplary displays illustrated in FIGS. 11-15.

One exemplary arrangement includes a button for initiating the determination of remaining time, increase button, decrease button, start/stop button, and toggle to switch between hours/minutes and minutes/seconds button. Another exemplary arrangement includes a button for initiating the determination of remaining time, increase button, decrease button, and start/stop button. Either exemplary arrangement could include a button/switch for switching between heating and cooling in embodiments with both features. The increase and decrease buttons, for example, can be used to set the temperature, a timer when not using the time remaining features (or in addition if a second timer is included), cycle through types of foods, and enter the weight of food depending upon the implementation.

In at least one exemplary embodiment, the interface 624 includes a keypad for entering temperature, weight, etc. in place of the increase and decrease buttons. The interface 624 in at least one exemplary embodiment includes an on/off switch/button. Alternatively, an on-off power switch may be provided separate from the interface 624.

Although the interface 624 is shown separate from the display 622, it is also possible to provide a display 622 that includes the user input function to be the interface 624 or to supplement elements dedicated to the interface 624. For example, the display 622 may be touch sensitive and responsive to a user's touch or a stylus and allow for the selection of various operational functions on the display itself.

The thermometer circuitry 626 includes means for performing the functional steps described above in connection with any one of the different exemplary methods such that it is capable of performing at least one of the described methods. In an exemplary embodiment, the working voltage for an integrated circuit that is a part of the thermometer circuitry 626 is 3 V.

An exemplary range for operation of the apparatus is in a temperature range between −40° C. to 300° C. or −40° F. to 572° F. Exemplary accuracy levels for measuring temperature are shown below:

| Temperature | Accuracy | Temperature | Accuracy |
| --- | --- | --- | --- |
| −40° C. to 0° C. | +/−2° C. | −40° F. to 32° F. | +/−4° F. |
| 0° C. to 150° C. | +/−1° C. | 32° F. to 302° F. | +/−2° F. |
| 150° C. to 177° C. | +/−2° C. | 302° F. to 350° F. | +/−4° F. |
| other ranges | +/−4° C. | other ranges | +/−8° F. |

Figure 7:
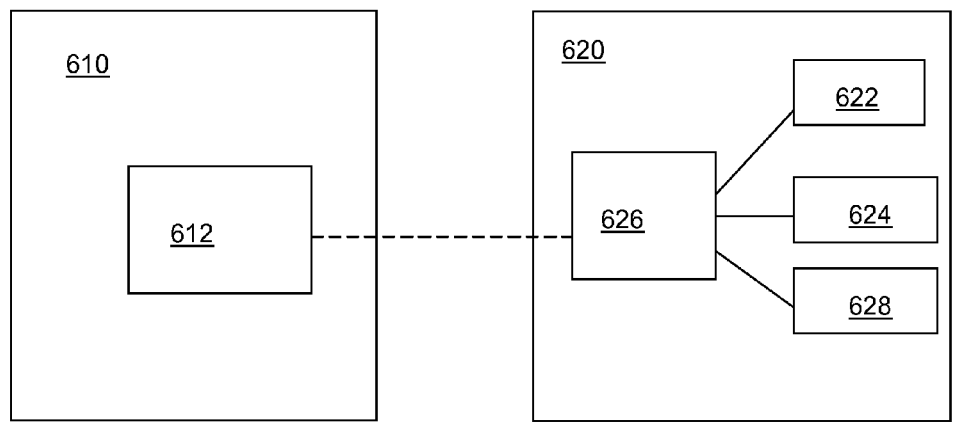
FIG. 7 illustrates a block diagram of an exemplary embodiment according to the invention.

FIG. 7 illustrates an exemplary apparatus similar to that shown in FIG. 6 with the addition of a sound system 628 driven by the thermometer circuitry 626. The sound system 628 includes a speaker that provides sound for various notifications and announcements as discussed above in connection with the exemplary methods. Examples include announcing the time remaining for the food to reach the desired temperature, spoken announcements such as "your food will be done in five minutes" and "the leftovers will be ready for the refrigerator in five minutes" with other time durations possible, and announcing other information relevant to the food including the internal temperature of food. The thermometer circuitry 626 includes the ability to generate the spoken announcements by including, for example, data-to-voice signal processing capability.

Figure 8:
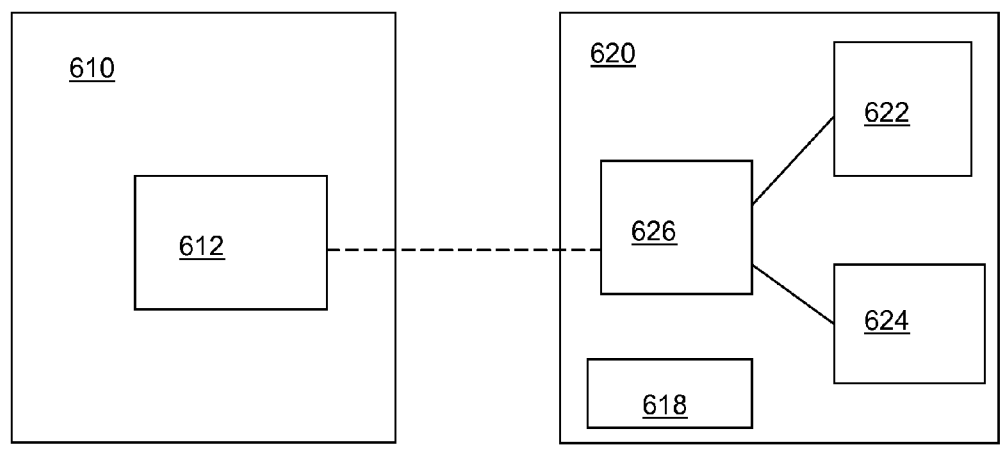
FIG. 8 illustrates a block diagram of an exemplary embodiment according to the invention.

FIG. 8 illustrates an exemplary apparatus similar to that shown in FIG. 6 with the addition of a second probe 618 or alternatively the temperature sensing component with out the other probe components. The second probe 618 is connected to the thermometer circuitry 626. The second probe 618 facilitates the reading of the environment temperature for cooling embodiments where the desired temperature is based on the room temperature.

Figure 9:
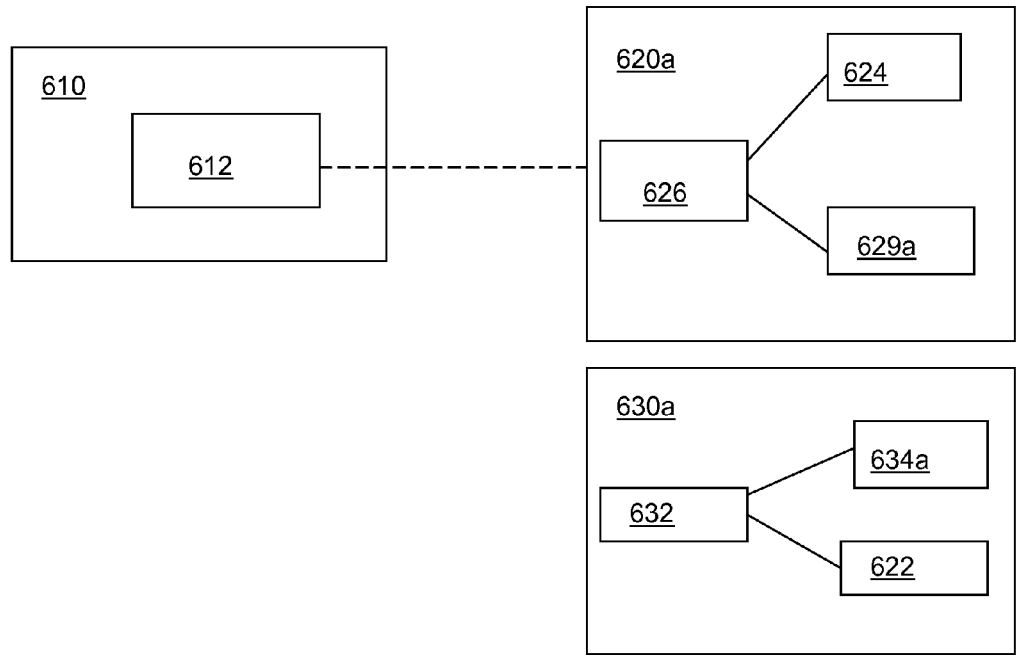
FIG. 9 illustrates a block diagram of an exemplary embodiment according to the invention.
Figure 10:
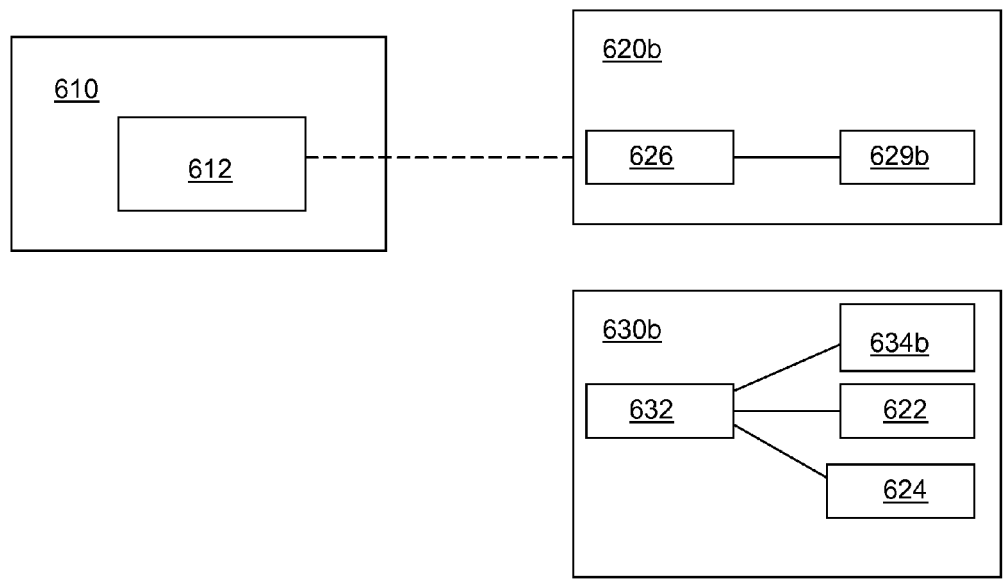
FIG. 10 illustrates a block diagram of an exemplary embodiment according to the invention.

FIGS. 9 and 10 illustrate exemplary systems where the components of the base unit are split into two units with the first unit in communication with the probe 610 and the second unit able to be remote from the first unit such as with the cook watching television or cooking/preparing other food for a meal. Although not illustrated, the first unit in at least one exemplary embodiment includes a display 622. Although not illustrated, the sound system 628 described in connection with FIG. 7 may be incorporated into the first unit and/or the second unit. The second probe 618 described in connection with FIG. 8 may be incorporated into the first unit.

FIG. 9 illustrates the first unit 620a with the interface 624, the thermometer circuitry 626, and a transmitter 629a. The illustrated second unit 630a includes the display 622, a processor 632 and a receiver 634a for communicating with the transmitter 629. The display 622 in this illustrated embodiment is driven by the processor 632 that receives a signal via the receiver 634a from the first unit 620a.

FIG. 10 illustrates an alternative to what is shown in FIG. 9. The illustrated first unit 620b includes the thermometer circuitry 626 and an antenna 629b. The illustrated second unit 630b includes the display 622, the interface 624, the processor 632, and an antenna 634b. The antennas 629b, 634b are bi-directional in that each is capable of transmitting and receiving information. Between the thermometer circuitry 626 and the processor 632 all of the processing and control is accomplished in this exemplary embodiment, and as such the processing load can be placed on either one. An example is that the thermometry circuitry 626 may process the signal received from the probe 610 and then transmit the temperature data to the second unit 630b for further processing. A further example is that the thermometry circuitry 626 does all of the processing with the processor 632 driving the display 622 and relaying instructions received via the interface 624 to the thermometer circuitry 626.

Although not illustrated in FIGS. 6-10, the display 622 and the interface 624 may be one component or the display 622 may include some interface aspects as discussed previously.

FIGS. 11-15 illustrate different exemplary configurations for display 622.

Figure 11:
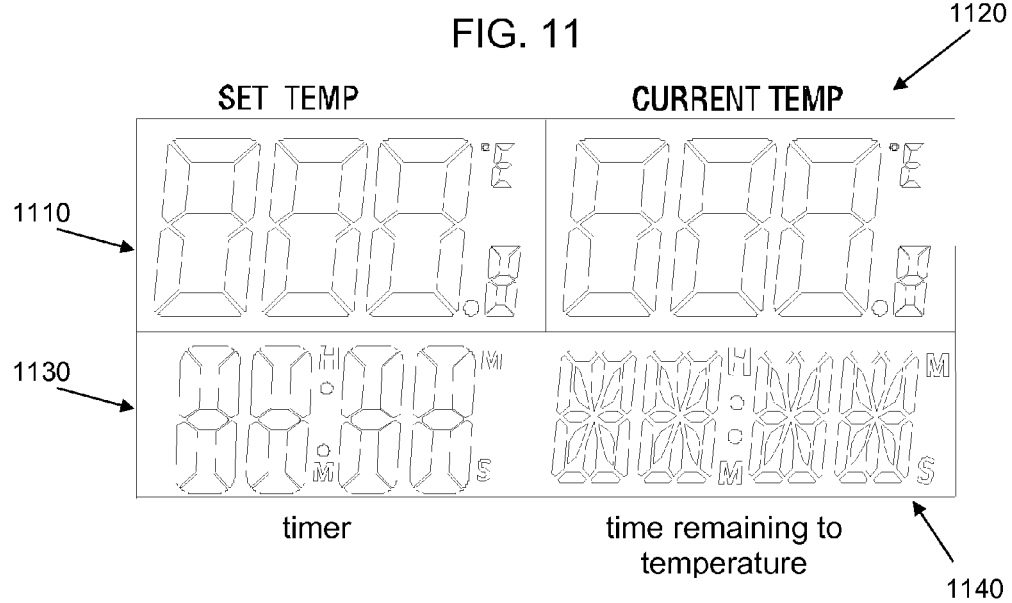
FIG. 11 illustrates an exemplary display for use in an exemplary embodiment according to the invention.

FIG. 11 illustrates an exemplary display arrangement for displaying the desired temperature 1110, the current temperature 1120, a general purpose timer 1130, and the time remaining until the desired temperature is reached 1140. The general purpose timer, for example, could utilize the Double:Time technology offered by F.O.B. Instruments, Hong Kong that allows the user to switch between hours:minutes to minutes:seconds. An exemplary interface includes a pair of buttons (or touch screen areas) for increasing and decreasing the value of the desired temperature setting and the timer value. In at least one exemplary embodiment, the depression of both buttons will toggle the temperature unit between Celsius and Fahrenheit; however, there could be a specific toggle button to perform this function. The exemplary interface also includes a start/stop button to deactivate any alarm/notification and operate the timer. The exemplary interface if the Double:Time technology is being used includes a button, a touch screen area, or other activation mechanism to toggle between the settings. The exemplary interfaces include an indication as to whether the temperatures are being displayed as Celsius or Fahrenheit.

Figure 12:
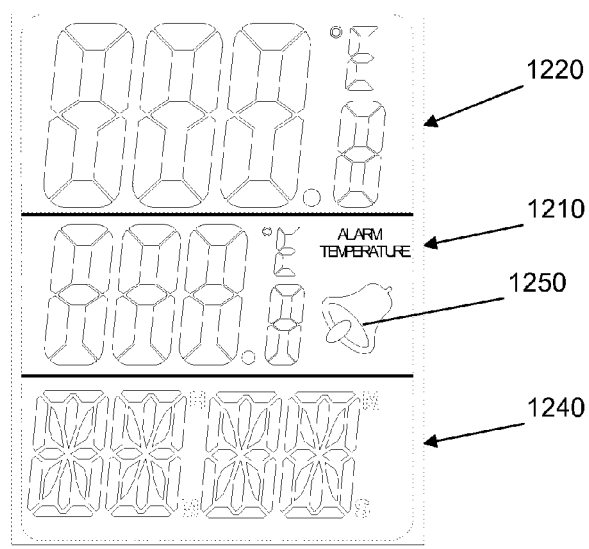
FIG. 12 illustrates an exemplary display for use in an exemplary embodiment according to the invention.

FIG. 12 illustrates an exemplary display arrangement that includes the desired temperature 1210, the current temperature 1220, and the time remaining to reach the desired temperature 1240. The illustrated display includes a bell image 1250 that is lit as part of notification(s). The interface would be similar to that described for the display illustrated in FIG. 11 with one difference being the Double:Time technology if present would be used to switch the display mode for the time remaining to cook.

Figure 13:
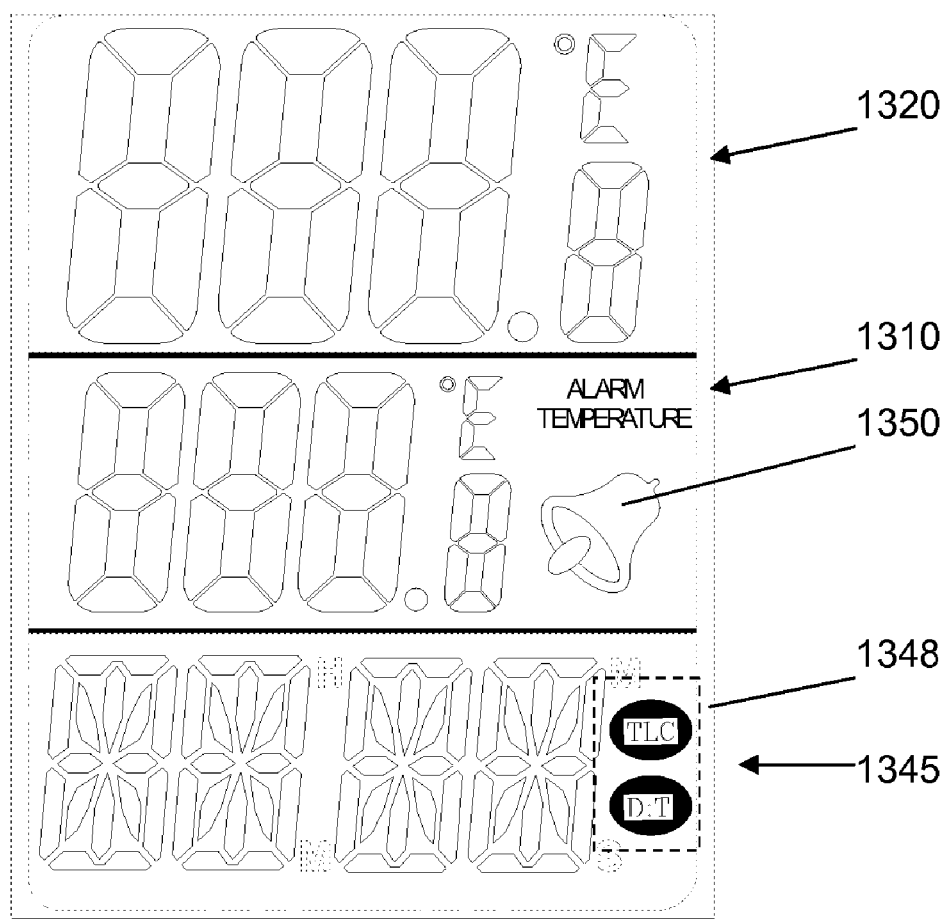
FIG. 13 illustrates an exemplary display for use in an exemplary embodiment according to the invention.

FIG. 13 illustrates an exemplary display arrangement that includes the desired temperature 1310, the current temperature 1320, and a timer area 1345. The timer area 1345 includes an indicator 1348 as to whether the timer 1345 is for the time remaining to reach a temperature is displayed or a general timer is displayed, which in this example the general timer is using the Double:Time technology although a generic timer could be used instead.

Figure 14:
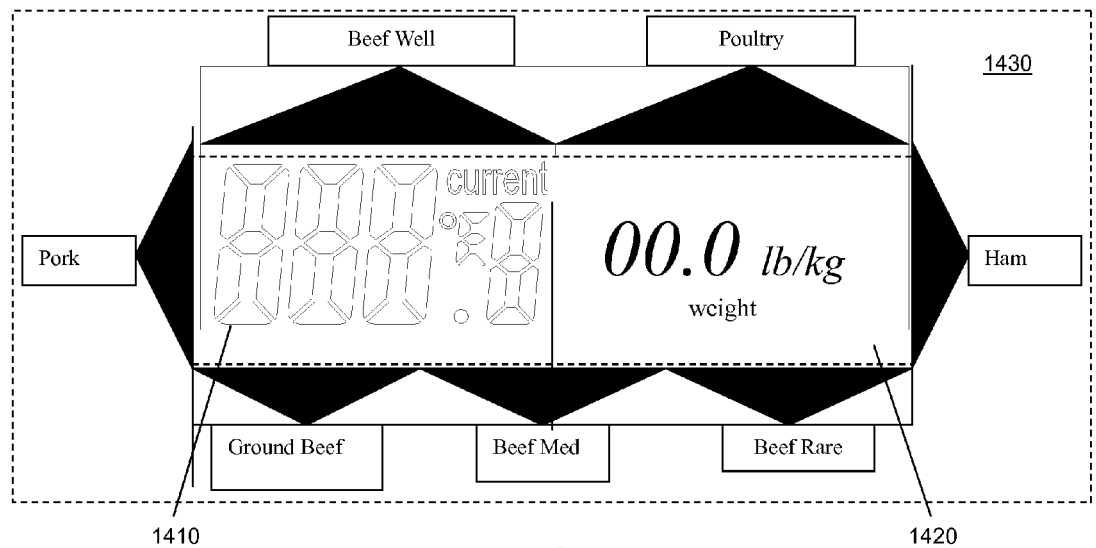
FIG. 14 illustrates an exemplary display for use in an exemplary embodiment according to the invention.
Figure 15:
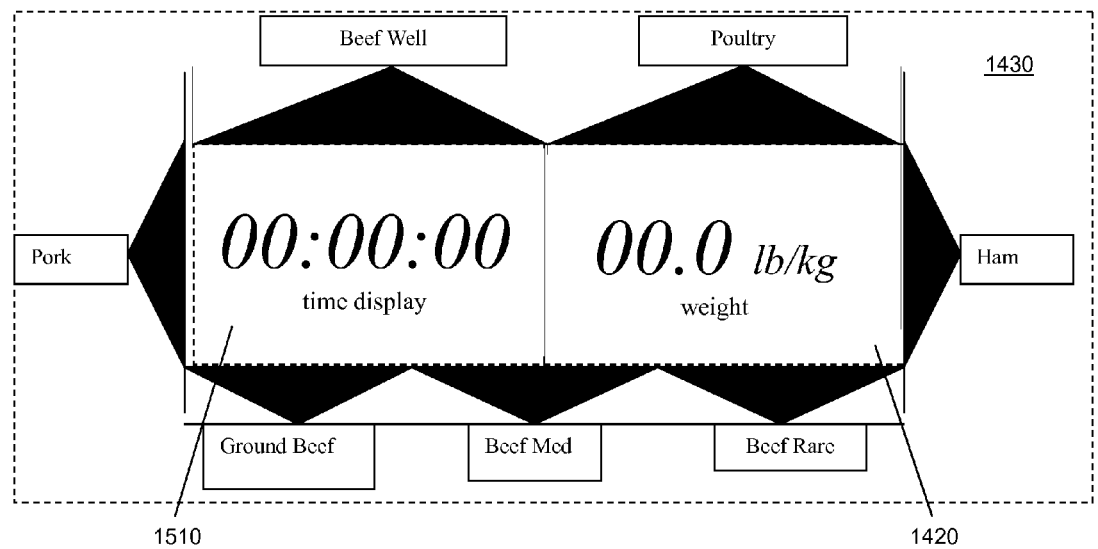
FIG. 15 illustrates an exemplary display for use in an exemplary embodiment according to the invention.

FIG. 14 illustrates an exemplary display showing the current temperature 1410, the weight of the food 1420, and the type of the meat 1430 that allows the user to enter the weight of the item being cooked and the type of food it is, for example, roast, steak, poultry, pork, etc. The illustrated type of meat indication (the elements bordered by the dashed lines) includes a plurality of light up arrows pointing at the meat with the selected meat being indicated by the lit arrow. Exemplary ways for the user to enter this information is with a keypad, a pair of buttons (or dial) for increasing and decreasing the weight and in at least embodiment the control circuit accelerates the scrolling through weights by for example skipping intermediary weights as the button is held down, or two sets of increasing and decreasing buttons (one set for whole pounds/kilograms and one set for fractions of pounds/kilograms). Optionally the device will include a toggle option to switch between pounds and kilograms similar to the Celsius/Fahrenheit toggle described above with its own button or use of a combination of other buttons or multipurpose button. Based on the type of food and its weight, the method determines the temperature needed to fully cook the food based upon stored information. A further embodiment is illustrated in FIG. 15, which replaces the temperature with a clock 1510 whose time period is determined by the meat selection such that it counts down from the cooking time or counts up to the cooking time. In at least one embodiment, an alarm or other notification is provided at the end of the cooking period. This exemplary embodiment can be combined with the above-described exemplary methods by having the desired temperature being obtained from previously stored information based on the entered weight and type of food.

Those having ordinary skill in the art will recognize that the state of the art has progressed to the point where there is little distinction between hardware and software implementations of aspects of apparatuses. Those having ordinary skill in the art will appreciate that there are various vehicles by which processes and/or systems described herein can be effected (for example, hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected.

The foregoing detailed description has set forth various embodiments of the devices and/or processes via the use of block diagrams, flowcharts, and examples. Insofar as such block diagrams, flowcharts, and examples contain one or more functions and/or operations, it will be understood by those within the art that each function and/or operation within such block diagrams, flowcharts, or examples can be implemented, individually and/or collectively, by a wide range of hardware, software, firmware, or any combination thereof (or means for performing the respective function and/or operation). However, those skilled in the art will recognize that the embodiments disclosed herein, in whole or in part, can be equivalently implemented in standard Integrated Circuits, via Application Specific Integrated Circuits (ASICs), as firmware, or as virtually any combination thereof, and that designing the circuitry and/or writing the code for the software or firmware would be well within the skill of one of ordinary skill in the art in light of this disclosure.

The exemplary embodiments described above may be combined in a variety of ways with each other. Furthermore, the dimensions, shapes, sizes, and number of the various pieces illustrated in the figures may be adjusted from that shown.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic. As used in this disclosure, "in communication" includes the situations where two pieces abut each other, are connected to each other including physically and wirelessly, engage each other, and integrally formed together as one piece.

Although the present invention has been described in terms of particular embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

We claim:

1. A method for predicting the time for an item to reach a desired temperature, said method comprising:
   obtaining a desired temperature;
   beginning an elapsed timer;
   determining a current temperature of an and item;
   calculating the predicted time until the item reaches the desired temperature based on the value of the elapsed timer and the percentage of temperature range between a first determined temperature and the desired temperature remaining to be covered; and
   repeating the determining and calculating steps with the desired temperature representing a desired cooling temperature.

2. The method according to claim 1, further comprising displaying the value of the predicted time.

3. The method according to claim 1, further comprising notifying the user when the current temperature of the item reaches the desired temperature.

4. The method according to claim 1, further comprising repeating the determining and calculating steps after a predetermined amount of temperature change.

5. The method according to claim 1, further comprising repeating the determining and calculating steps at predetermined intervals.

6. The method according to claim 1, further comprising repeating the determining and calculating steps continually until the desired temperature is reached.

7. The method according to claim 1, further comprising when predicting time remaining during a cooling cycle,
   tracking the time spent cooling from an upper threshold, and
   notifying the user, when the sum of the time spent cooling added to the time remaining to reach the desired temperature exceeds a predetermined cooling time.

8. The method according to claim 1, wherein the item is food, the method further comprising:
   receiving identification of the food, and
   receiving a weight of the food,
   wherein calculating the time is based on at least the desired temperature, the current temperature, the identification of the food, and the weight of the food.

9. The method according to claim 1, further comprising:
   notifying the user when the temperature read is within a first range including 32° F.,
   receiving a calibration instruction from the user when the temperature is within the first range, and
   storing an error value such that the temperature measured is equivalent to 32° F.

10. The method according to claim 1, further comprising receiving an instruction to predict the time to cool the item to a desired cooling temperature, and
   repeating the beginning, determining, and calculating steps for the desired temperature equal to the received desired cooling temperature.

11. The method according to claim 1, further comprising:
   monitoring the current temperature until it reaches its high point,
   recording the high temperature,
   monitoring the temperature change until the temperature change approximates a predetermined amount before restarting the elapsed timer.

12. The method according to claim 1, wherein the predicted time is calculated according to the formula $$t_R = \frac{t}{1 - \left(\frac{T_D - T_2}{T_D - T_1}\right)} \times \left(\frac{T_D - T_2}{T_D - T_1}\right)$$

$t_R$ equals the cooking time to reach the desired temperature, $T_D$ represents the desired temperature, $T_1$ equals an initial temperature, $T_2$ equals the current temperature with t representing the value of the elapsed timer.

13. The method according to claim 12, further comprising when predicting time remaining during cooling,
   tracking the time spent cooling, and
   notifying the user when the sum of the time spent cooling and the time remaining to reach the desired temperature exceeds a predetermined cooling time.

14. The method according to claim 1, further comprising starting a countdown timer having a value equal to the predicted time.

15. The method according to claim 14, further comprising notifying a user when the countdown timer reaches zero or when the current temperature is within a predetermined range of the desired temperature.

16. The method according to claim 14, further comprising notifying a user when the countdown timer reaches zero.

17. A method comprising:
   obtaining a desired temperature;
   beginning an elapsed timer;
   determining a current temperature of food being cooled including an initially determined temperature reading;
   calculating the predicted cooling time for food to reach the desired temperature based at least on the value of the elapsed timer and the current temperature; and
   repeating the determining and the calculating steps wherein the predicted cooling time is calculated based on a rate of temperature change determined subsequent to the initially determined temperature reading.

18. The method according to claim 17, further comprising starting a countdown timer from the predicted cooling time.

19. The method according to claim 17, further comprising displaying the predicted cooling time on a display.

20. The method according to claim 17, wherein the predicted cooling time is calculated based on the percentage of temperature range between the first determined temperature and the desired temperature remaining to be covered.

21. The method according to claim 17, wherein the predicted cooling time is calculated based on the percentage of temperature range between the first determined temperature and the desired temperature remaining completed.

22. The method according to claim 17, further comprising repeating the determining and calculating steps such that the period of time between repeated steps is a sampling period, and wherein the predicted cooling time is calculated based on a rate of temperature change over the last sampling period.

23. The method according to claim 17, wherein the predicted cooling time is calculated according to the formula $$t_R = \frac{t}{1 - \left(\frac{T_D - T_2}{T_D - T_1}\right)} \times \left(\frac{T_D - T_2}{T_D - T_1}\right)$$

$t_R$ equals the cooking time to reach the desired temperature, $T_D$ represents the desired temperature, $T_1$ equals an initial temperature, $T_2$ equals the current temperature with t representing the value of the elapsed timer.

24. The method according to claim 17, wherein the predicted cooling time is calculated according to the formula $$t_R = \frac{t}{\left(\frac{T_1 - T_2}{T_1 - T_D}\right)} \times \left(1 - \left(\frac{T_1 - T_2}{T_1 - T_D}\right)\right)$$

$t_R$ equals the cooking time to reach the desired temperature, $T_D$ represents the desired temperature, $T_1$ equals an initial temperature, $T_2$ equals the current temperature with t representing the value of the elapsed timer.

25. The method according to claim 17, wherein the predicted cooling time is calculated according to the formula $$t_R = \left(\frac{T_D - T_2}{T_2 - T_1}\right) \times (t_2 - t_1)$$

$t_R$ equals the cooking time to reach the desired temperature, $T_D$ represents the desired temperature, $T_1$ equals an initial temperature, $T_2$ equals the current temperature with t representing the value of the elapsed timer.

26. The method according to claim 17, wherein the elapsed timer is started at a threshold temperature, and the predicted cooling time is calculated based on the threshold temperature.

27. The method according to claim 26, further comprising notifying the user when the value of the elapsed timer exceeds a predetermined time amount.

28. The method according to claim 26, further comprising notifying the user when the value of the elapsed timer exceeds two hours.

29. The method according to claim 26, wherein the threshold temperature is 140° F.

30. The method according to claim 26, wherein the threshold temperature is 135° F.

31. The method according to claim 26, wherein the threshold temperature is the highest determined temperature for the food.

32. The method according to claim 26, wherein the threshold temperature is a previously desired cooking temperature for the food.

33. The method according to claim 26, further comprising notifying the user when the sum of the value of the elapsed timer and the calculated cooling time exceeds a predetermined time amount.

34. The method according to claim 26, further comprising notifying the user when the sum of the value of the elapsed timer and the calculated cooling time exceeds two hours.

35. The method according to claim 17, wherein the elapsed timer is started when the temperature of the food is 140° F., said method further comprising notifying the user when the value of the elapsed timer exceeds two hours and the temperature of the food is greater than or equal to the desired temperature.

36. The method according to claim 35, wherein the desired temperature equals 70° F.

37. The method according to claim 35, wherein the desired temperature equals approximately 70° F.

38. The method according to claim 35, wherein the desired temperature equals room temperature.

39. The method according to claim 35, wherein the desired temperature equals room temperature plus at least five degrees.

40. The method according to claim 35, wherein the desired temperature equals the higher value selected from 70° F. and room temperature.

41. The method according to claim 17, wherein the elapsed timer is started when the temperature of the food is 135° F., said method further comprising notifying the user when the value of the elapsed timer exceeds two hours and the temperature of the food is greater than or equal to the desired temperature.

42. The method according to claim 41, wherein the desired temperature equals 70° F.

43. The method according to claim 41, wherein the desired temperature equals approximately 70° F.

44. The method according to claim 41, wherein the desired temperature equals room temperature.

45. The method according to claim 41, wherein the desired temperature equals room temperature plus at least five degrees, 46. The method according to claim 41, wherein the desired temperature equals the higher value selected from of 70° F. and room temperature.

* * * * *